(12) United States Patent
Wen et al.

(10) Patent No.: US 11,717,246 B2
(45) Date of Patent: Aug. 8, 2023

(54) METHOD TO GENERATE LOCALIZER RADIOGRAPH BY ROTATING PROJECTIONS WITH FAN BEAM

(71) Applicant: Siemens Healthcare GmbH, Erlangen (DE)

(72) Inventors: Xiang Wen, Shanghai (CN); Yi Tian, Shanghai (CN); Tao Tao Li, Shanghai (CN); Guo Qing Zhang, Shanghai (CN); Wen Hao Chen, Shanghai (CN)

(73) Assignee: Siemens Healthcare GmbH, Erlangen (DE)

( * ) Notice: Subject to any disclaimer, the term of this patent is extended or adjusted under 35 U.S.C. 154(b) by 154 days.

(21) Appl. No.: 17/192,432

(22) Filed: Mar. 4, 2021

(65) Prior Publication Data
US 2021/0275122 A1 Sep. 9, 2021

(30) Foreign Application Priority Data

Mar. 5, 2020 (CN) .......................... 202010146061.4

(51) Int. Cl.
A61B 6/00 (2006.01)
G06T 11/00 (2006.01)
A61B 6/03 (2006.01)

(52) U.S. Cl.
CPC ............ *A61B 6/488* (2013.01); *G06T 11/005* (2013.01); *A61B 6/032* (2013.01); *A61B 6/4258* (2013.01); *G06T 2211/436* (2013.01)

(58) Field of Classification Search
CPC ........... A61B 6/03; A61B 6/032; A61B 6/541; A61B 6/488; A61B 6/463; A61B 5/318; A61B 6/503; A61B 6/542; A61B 6/465; A61B 6/027; A61B 6/548; A61B 6/4007; A61B 6/486; A61B 6/544; A61B 6/4078; A61B 6/0407; A61B 6/5205; A61B 6/545; A61B 6/035; A61B 6/5235; A61B 6/44; A61B 6/037; A61B 6/4417; A61B 5/055; A61B 5/0037; A61B 6/04; A61B 8/40;
(Continued)

(56) References Cited

U.S. PATENT DOCUMENTS 5,524,130 A 6/1996 Ohhashi
7,822,171 B2 * 10/2010 Bontus .................. A61B 6/027
378/11
(Continued)

FOREIGN PATENT DOCUMENTS

JP H06121794 A 5/1994
JP 2002186612 A 7/2002
(Continued)

*Primary Examiner* — Irakli Kiknadze
(74) *Attorney, Agent, or Firm* — Banner & Witcoff Ltd.

(57) ABSTRACT

In a medical image generation method, projection data of a scanned object is acquired during rotation of a radiographic source, and a scout image of the scanned object is generated in one scanning direction using corresponding projection data in two opposite scanning directions in the projection data. The scanning direction is used to represent a relative position relationship between the radiographic source and the scanned object. Using projection data in two opposite directions to generate a scout image in one direction during rotary scanning of a radiographic source can significantly shorten the generation time of the scout image.

15 Claims, 10 Drawing Sheets

(58) Field of Classification Search
CPC .. A61B 8/54; A61B 6/54; A61B 5/704; A61B 6/0492; A61B 5/1079; A61B 6/4258; A61B 6/4085; A61B 6/482; A61B 6/5294; A61B 6/466; A61B 6/5217; A61B 6/481; A61B 5/7207; A61B 5/349; A61N 5/1081; A61N 5/1084; G06T 11/005; G06T 7/0012; G06T 2211/436; G06T 2211/408; G06T 2211/424; G16H 40/60; G16H 50/50; G01R 33/543; G06F 16/5838; G01N 23/046; G01N 2223/419; G01N 2223/612
USPC ...................................................... 378/19, 20
See application file for complete search history.

(56) References Cited

U.S. PATENT DOCUMENTS

| | | | | |
|---|---|---|---|---|
| 8,031,828 | B1* | 10/2011 | DeMan | G06T 11/005 378/4 |
| 9,420,976 | B2* | 8/2016 | Jackson | A61B 6/06 |
| 10,561,391 | B2* | 2/2020 | Nett | A61B 6/027 |
| 10,639,415 | B2* | 5/2020 | Yi | A61M 5/007 |
| 2005/0152493 | A1* | 7/2005 | Seto | A61B 6/542 378/20 |

FOREIGN PATENT DOCUMENTS

| | | |
|---|---|---|
| JP | 2007159878 A | 6/2007 |
| JP | 2009089810 A | 4/2009 |

* cited by examiner

METHOD TO GENERATE LOCALIZER RADIOGRAPH BY ROTATING PROJECTIONS WITH FAN BEAM

CROSS REFERENCE TO RELATED APPLICATIONS

This patent application claims priority to Chinese Patent Application No. 202010146061.4, filed Mar. 5, 2020, which is incorporated herein by reference in its entirety.

BACKGROUND

Field

The present application relates to the medical imaging field, and in particular relates to a medical image generation method, apparatus and system.

Related Art

Some medical imaging technologies generate a medical image of a scanned object by rotating a radiographic source and moving a scanning table. A scout scan is usually required before a formal scan so as to obtain the position and size of a scanned object on a scanning table and determine the range and dose for the formal scan. Currently, it usually takes a scout scan a long time to use projection data obtained at a preset angle of a radiographic source to generate a scout image at the angle. In addition, a position deviation of the scanned object will lead to a great scout image error.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
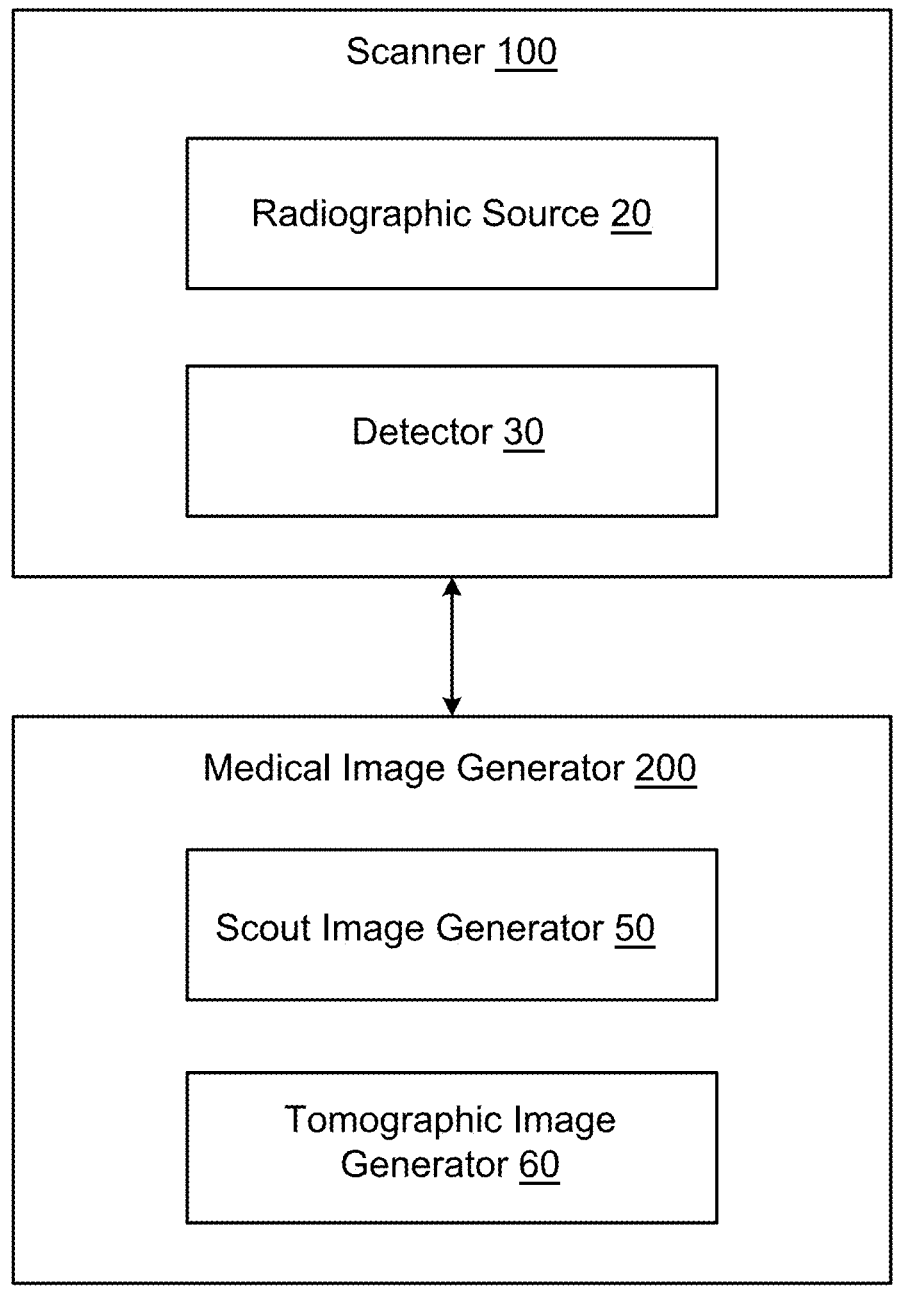
FIG. 1 is a schematic diagram of a medical image generation system according to an exemplary embodiment.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the present disclosure is to provide a medical image generation method, apparatus and system to speed up the generation of a scout image.

The medical image generation method provided by the embodiments of the present application comprises: acquiring projection data of a scanned object during the rotation of a radiographic source, and using corresponding projection data in two opposite scanning directions in the projection data to generate a scout image of the scanned object in one scanning direction, wherein the scanning direction is used to represent the relative position relationship between the radiographic source and the scanned object.

The embodiments further provide a medical image generation apparatus and the apparatus comprises: a data acquisition module, configured to acquire projection data of a scanned object during the rotation of a radiographic source, and an image generation module, configured to use corresponding projection data in two opposite scanning directions in the projection data to generate a scout image of the scanned object in one scanning direction, wherein the scanning direction is used to represent the relative position relationship between the radiographic source and the scanned object.

It can be seen that using projection data in two opposite directions to generate a scout image in one direction during rotary scanning of a radiographic source can significantly shorten the generation time of the scout image.

In some embodiments, using corresponding projection data in two opposite scanning directions in the projection data to generate a scout image of the scanned object in one scanning direction may comprise: extracting corresponding equivalent projection data in a second scanning direction from corresponding projection data in a first direction range of a first scanning direction and inserting the equivalent projection data into corresponding projection data in the second scanning direction, wherein the second scanning direction is opposite to the first scanning direction.

In this way, equivalent projection data is extracted from corresponding projection data in the range of one direction opposite to the target scanning direction to simulate the projection data in the target scanning direction, and the image quality of the scout image is improved.

In some embodiments, extracting corresponding equivalent projection data in a second scanning direction from corresponding projection data in a first direction range of a first scanning direction may comprise: for a plurality of scanning directions in the first direction range, extracting corresponding line projection data of one ray sub-beam from corresponding projection data in each scanning direction of the plurality of scanning directions, wherein the ray sub-beam is a collection of rays of the ray beam emitted from the radiographic source in the scanning direction, with the included angle between the projection of the rays on the plane of the gantry and the plane where the scanning table is located within a preset angle range, and re-sorting the extracted line projection data to obtain the equivalent projection data.

In this way, in the range of the direction opposite to the target direction, by selecting ray sub-beams in a specific angle range respectively from a plurality of ray beams emitted from the radiographic source, projection data of ray beams emitted from the radiographic source in any required shape can be simulated to meet the requirements in different situations.

In some embodiments, extracting corresponding line projection data of one ray sub-beam from corresponding projection data in the scanning direction may comprise: extracting line projection data of a corresponding ray sub-beam in one angle sub-range of the angle range covered a ray beam emitted from the radiographic source in the second scanning direction from corresponding projection data in the scanning direction, wherein the plurality of scanning directions correspond to different angle sub-ranges, respectively.

It can be seen that the extracted ray sub-beams respectively correspond to the ray sub-beams of the ray beams, emitted from the radiographic source in the target scanning direction, in different directions. Therefore, projection data obtained when the radiographic source scans in the scanning direction can be simulated. Thus, the image quality of the obtained scout image is equivalent to the quality of the scout image generated by use of a traditional method.

In some embodiments, extracting corresponding line projection data of one ray sub-beam from corresponding projection data in the scanning direction may comprise: extracting corresponding line projection data of ray sub-beams having the same preset angle range respectively from corresponding projection data in the plurality of scanning directions.

In this way, the distortion of the scanned object in the scout image can be reduced by extracting corresponding projection data of near-parallel ray sub-beams.

In some embodiments, re-sorting the extracted line projection data comprises: re-sorting the extracted corresponding point projection data of points of each ray sub-beam in a reverse order, and re-sorting the projection data of each ray sub-beam in the corresponding order of the ray sub-beams in a second scanning direction.

It can be seen that since the scanning direction is different, the order of projection data is different and the order of the ray sub-beams extracted from ray beams in different scanning directions is also different from the order of the ray sub-beams of the simulated ray beam in the target direction. Equivalent projection data in the target direction can correctly be reconstructed by re-sorting the projection data.

In some embodiments, the method may further comprise: extracting corresponding recombined projection data in a second scanning direction as corresponding projection data in the second scanning direction from corresponding projection data in a second direction range of the second scanning direction.

In this way, by extracting corresponding projection data at the required ray angle from projection data of a plurality of ray beams in the direction range of one target scanning direction, ray beams emitted from the radiographic source in the target scanning direction in any shape can be simulated to meet different requirements.

In some embodiments, extracting corresponding recombined projection data in a second scanning direction comprises: for a plurality of scanning directions in a second direction range of the second scanning direction, extracting corresponding second line projection data of one ray sub-beam respectively from corresponding projection data in each scanning direction of the plurality of scanning directions, wherein the ray sub-beam is a collection of rays of the ray beam emitted from the radiographic source in the scanning direction, with the included angle between the projection of the rays on the plane of the gantry and the plane where the scanning table is located within a preset angle range, and combining second line projection data to obtain the recombined projection data.

In this way, the distortion of the scanned object in the scout image can be reduced by extracting corresponding projection data of parallel ray sub-beams.

In some embodiments, the same angle range is centered at the second scanning direction.

In this way, a size deviation brought about by divergent ray beams to the scanned object in the scout image when the position of the scanned object deviates from the rotating center of the radiographic source may be avoided.

In some embodiments, inserting the simulated projection data into corresponding projection data in the second scanning direction comprises: arranging the equivalent projection data and the corresponding projection data in the second scanning direction in the order of the scan time of the data.

In this way, a scout image covering an expected scanning range may be generated and the generation time of the scout image may be shortened.

In some embodiments, the method may further comprise: inserting interpolation data calculated according to the equivalent projection data and corresponding projection data in the second scanning direction in a position where the equivalent projection data and the projection data in the second scanning direction are spliced.

In this way, by interpolating values in the areas not covered by projection data in two opposite directions, the generation time of a scout image may be further shortened.

In some embodiments, the method may further comprise: modulating the current supplied to the radiographic source to control the intensity of rays emitted from the radiographic source in a preset first direction range of the first scanning direction and a second direction range of the second scanning direction greater than the intensity of rays emitted in directions beyond the first direction range and the second direction range.

It can be seen that the intensity of the rays in the direction range where no projection data needs to be acquired is low. Thus, the radiation dose a scanned object receives during a scout scan is reduced and the influence of radiation on the health of the scanned object is alleviated.

The embodiments further provide a medical image generation apparatus and the apparatus comprises a processor and a memory, wherein computer-readable instructions are stored in the memory and the instructions enable the processor to execute the method provided by the embodiments.

The embodiments further provide a medical image generation system and the system comprises: a scanning apparatus, configured to acquire projection data of a scanned object during the rotation of a radiographic source, and an image generation apparatus, configured to execute the method provided by the embodiments to generate a scout image of the scanned object.

The embodiments further provide a computer-readable storage medium, computer-readable instructions are stored in the computer-readable storage medium, and the instructions enable one or more processors to execute the methods provided the embodiments.

FIG. 1 is a schematic diagram of a medical image generation system. As shown in FIG. 1, the medical image system comprises a scanning apparatus (scanner) 100 and a medical image generation apparatus 200.

The scanning apparatus 100 is an apparatus which performs a scan to obtain projection data. The scanning apparatus 100 may comprise a radiographic source 20 and a detector 30, for example. The radiographic source 20 may emit ray beams, which are received by the detector 30 after passing a scanned object. The radiographic source 20 may be an X-ray generation apparatus or γ-ray generation apparatus. The detector 30 is a detector array and is used to convert detected rays into projection data.

The medical image generation apparatus 200 utilizes projection data acquired by the detector 30 to generate medical images. The medical image generation apparatus 200 can comprise a scout image generator 50 and a tomographic image generator 60. The scout image generator 50 may utilize digital signals produced during a scout scan to generate a scout image. The tomographic image generator 60 can utilize digital signals produced during a tomographic scan to generate a tomographic image.

Figure 2:
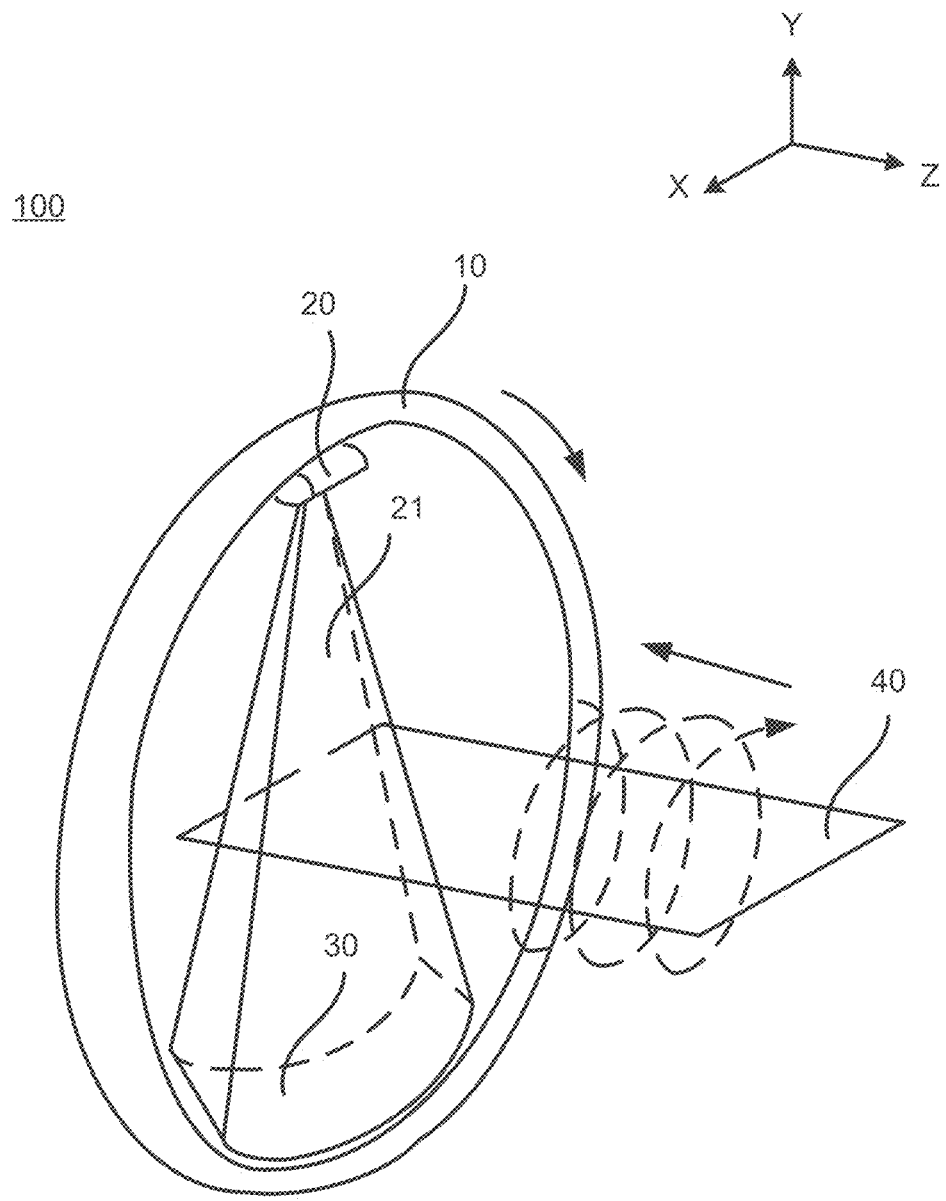
FIG. 2 is a schematic diagram of a scanning apparatus according to an exemplary embodiment.

FIG. 2 is a schematic diagram of a scanning apparatus. As shown in FIG. 2, the scanning apparatus 100 comprises a gantry 10, a radiographic source 20, a detector 30 and a scanning table 40.

The radiographic source 20 and the detector 30 are both fixed on the gantry 10 and can rotate together with the gantry 10.

The scanning table 40 is used to bear a scanned object and can move in the direction of the axis of rotation.

For a tomographic scan, in the example in FIG. 2, the gantry 10 can rotate in the direction shown in the figure around the Z-axis, and the scanning table 40 can move in the negative direction of the Z-axis to enter the scanning area. During rotations, the radiographic source 20 emits a ray beam 21. After passing a scanned object on the scanning table 40, the ray beam 21 is received by the detector 30 and is converted into digital signals. That is to say, the scanning process is equivalent to a spiral scan performed for a scanned object in the direction indicated by the spiral line in the figure when the scanning table 40 is fixed.

For a scout scan, one way is to adopt static scanning, that is to say, the scanning table 40 moves, the gantry 10 does not rotate, and the radiographic source 20 is fixed at a required exposure angle when the scanned object is scanned. Since the gantry 10 needs to rotate for a tomographic scan, the gantry 10 needs to be sped up after a scout scan so that the gantry is switched from a static state to a rotational state to perform the tomographic scan, and for a next scanned object, the gantry 10 needs to be slowed down so that it is switched from a high-speed rotational state to a static state. The frequent switchover from a rotational state to a static state and to a rotational state will lead to a long check time and reduce the service life of the component. Another way is to perform a scout scan when the gantry 10 is in a rotational state and utilize the projection data acquired each time the radiographic source 20 passes the required exposure angle to generate a scout image. This way requires a seamless joint of a scanned area each time the radiographic source 20 passes the exposure angle. Since the scanning table 40 moves slowly, it is slow and time-consuming to generate a scout image.

Figure 3:
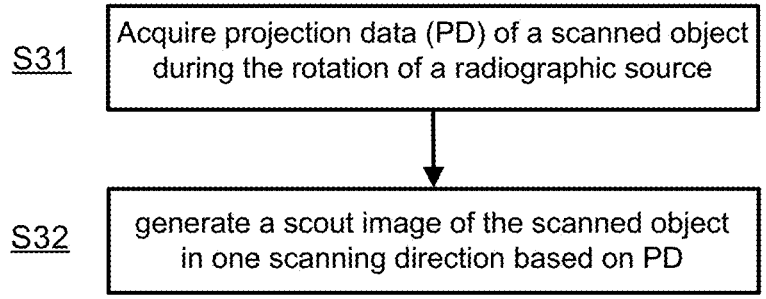
FIG. 3 is a flowchart of a medical image generation method according to an exemplary embodiment.

The embodiments of the present application provide a medical image generation method in which projection data produced when a radiographic source scans in two opposite directions is utilized to generate a scout image, and thus the generation of the scout image is sped up. FIG. 3 is a flowchart of a medical image generation method in the embodiments of the present application.

As shown in FIG. 3, the method comprises the following steps: Step S31: Acquire projection data of a scanned object during the rotation of a radiographic source 10, and Step S32: Use corresponding projection data in two opposite scanning directions in the projection data to generate a scout image of the scanned object in one scanning direction.

The scanning direction is used to represent the relative position relationship between the radiographic source and the scanned object. Since a ray beam emitted from the radiographic source 20 usually consists of a plurality of divergent rays, for the convenience of description, the direction of rays at the center of the ray beam emitted from the radiographic source 20 or the direction of a vertical line from the center of the radiographic source 20 to the axis of rotation of the radiographic source 20 can be used to represent a scanning direction.

A scanned object can be the body, or organs or specific parts of a human being or animal. Projection data depicts a data array. The data array corresponds to the sensor array in the data detector 30, and each sensor produces data of one point.

Since a scanned object has the same ray penetrability effect in two opposite directions, back projection data and forward projection data can be used together to generate a scout image at a required angle. Compared with using only projection data in one direction to generate a scout image, using projection data in two opposite directions can allow a high rotation speed of the gantry and/or a high moving speed of the scanning table, and thus can significantly shorten the generation time of the scout image.

Here, "forward" and "back" are used to simply represent a target scanning direction and an opposite scanning direction, and may be used to represent a direction range or angle range, instead of a specific direction or angle.

Figure 4:
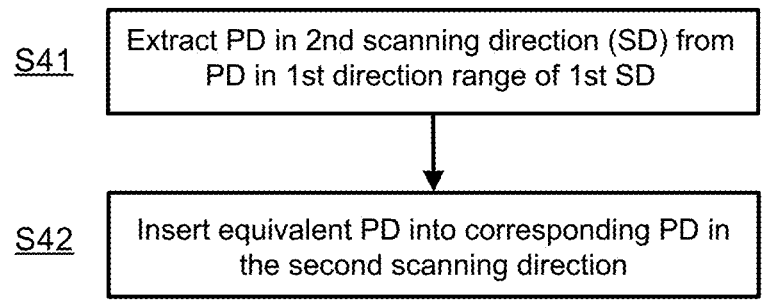
FIG. 4 is a flowchart of a medical image generation method according to an exemplary embodiment.

When projection data in two opposite scanning directions is used to generate a scout image, processing of back projection data can improve the image quality of the scout image in consideration of the paths of different rays of a back ray beam. FIG. 4 is a flowchart of another medical image generation method in the embodiments of the present application. As shown in FIG. 4, the method comprises the following steps: Step S41: Extract corresponding equivalent projection data in a second scanning direction from corresponding projection data in a first direction range of a first scanning direction.

Step S42: Insert equivalent projection data into corresponding projection data in the second scanning direction.

Here, the second scanning direction is the corresponding scanning direction of the required scout image, and is also known as target direction. The first scanning direction is opposite to the second scanning direction. The first direction range of the first scanning direction is a preset direction range including the first scanning direction and is used to extract corresponding equivalent projection data in a target scanning direction. The first direction range may be determined according to the required shape of a scanning ray beam.

Figure 5:
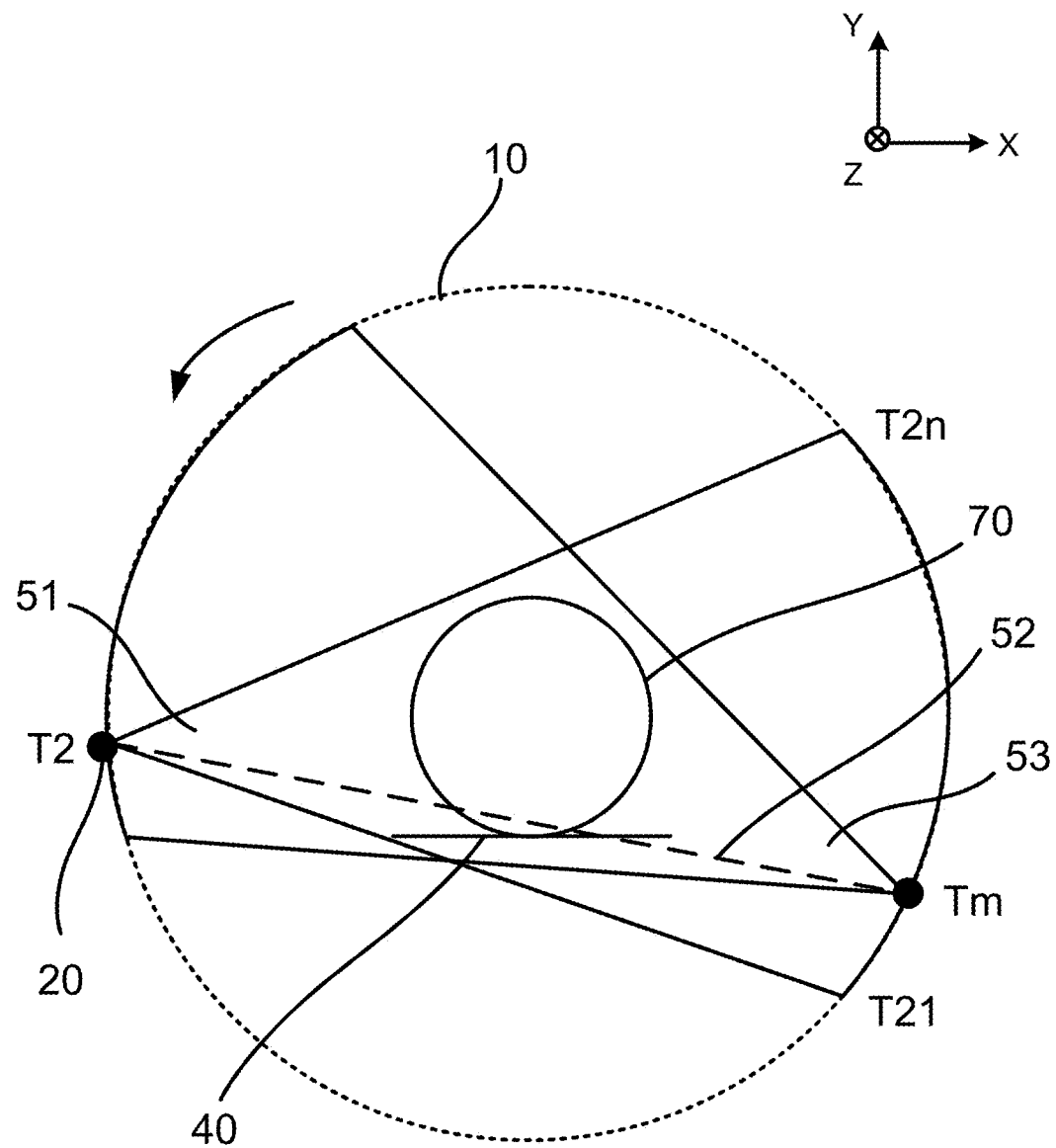
FIG. 5 is a schematic diagram of the extraction of equivalent projection data from back projection data according to an exemplary embodiment.

Equivalent projection data is projection data obtained by utilizing back projection data and used to simulate the forward scanning effect, and the projection effect of equivalent projection data is similar to the forward projection effect. FIG. 5 is a schematic diagram of the extraction of equivalent projection data from back projection data in the embodiments of the present application. As shown in FIG. 5, when a scout scan is performed, the gantry 10 rotates counterclockwise and the scanned object 70 moves together with the scanning table 40 in a direction opposite to the Z-axis. It is assumed that the target scanning direction is the direction indicated by the ray beam 51 emitted from the radiographic source 20. The ray beam 51 comprises a plurality of rays radiating in different directions. The ray beam 53 emitted from the radiographic source 20 in another position comprises a ray 52, which has the same angle as one ray of the ray beam 51 does. That is to say, when the ray 52 overlaps one ray of the ray beam 51 in space, their corresponding projection data is consistent. Similarly, a ray whose direction is consistent with the direction of a ray of the ray beam 51, for example, the ray 52 emitted at the time point Tm, can be found in each ray beam emitted from the radiographic source 20 between the time point T21 and the time point T2n. Therefore, equivalent projection data can be extracted from the projection data between the time point T21 and the time point T2n to simulate the projection data produced by the ray beam emitted from the radiographic source in the time range of T21 to T2n. "To simulate" here means obtaining projection data of ray beams which actually do not exist and are emitted in the target scanning direction at the time point T20. "Equivalent projection data" here is actually not completely consistent with the projection data produced by the ray beam in the target scanning direction because the corresponding Z-axis position of each ray beam emitted between the time point T21 and the time point T2n is different. "Equivalent projection data" obtained by combining projection data in which Z-axis positions are slightly different is a simulation of projection data produced by a distorted ray beam in the target scanning direction. For example, the projection produced by a ray beam emitted from the radiographic source 20 is a rectangle, and the corresponding projection of the equivalent projection data extracted from a plurality of ray beams in the opposite direction may be a parallelogram; for equivalent projection data whose projection is a parallelogram, data can be extracted from other data to patch the parallelogram into a rectangle, or some of equivalent projection data may be discarded to cut the parallelogram into a rectangle to obtain the finally used equivalent projection data.

Figure 6:
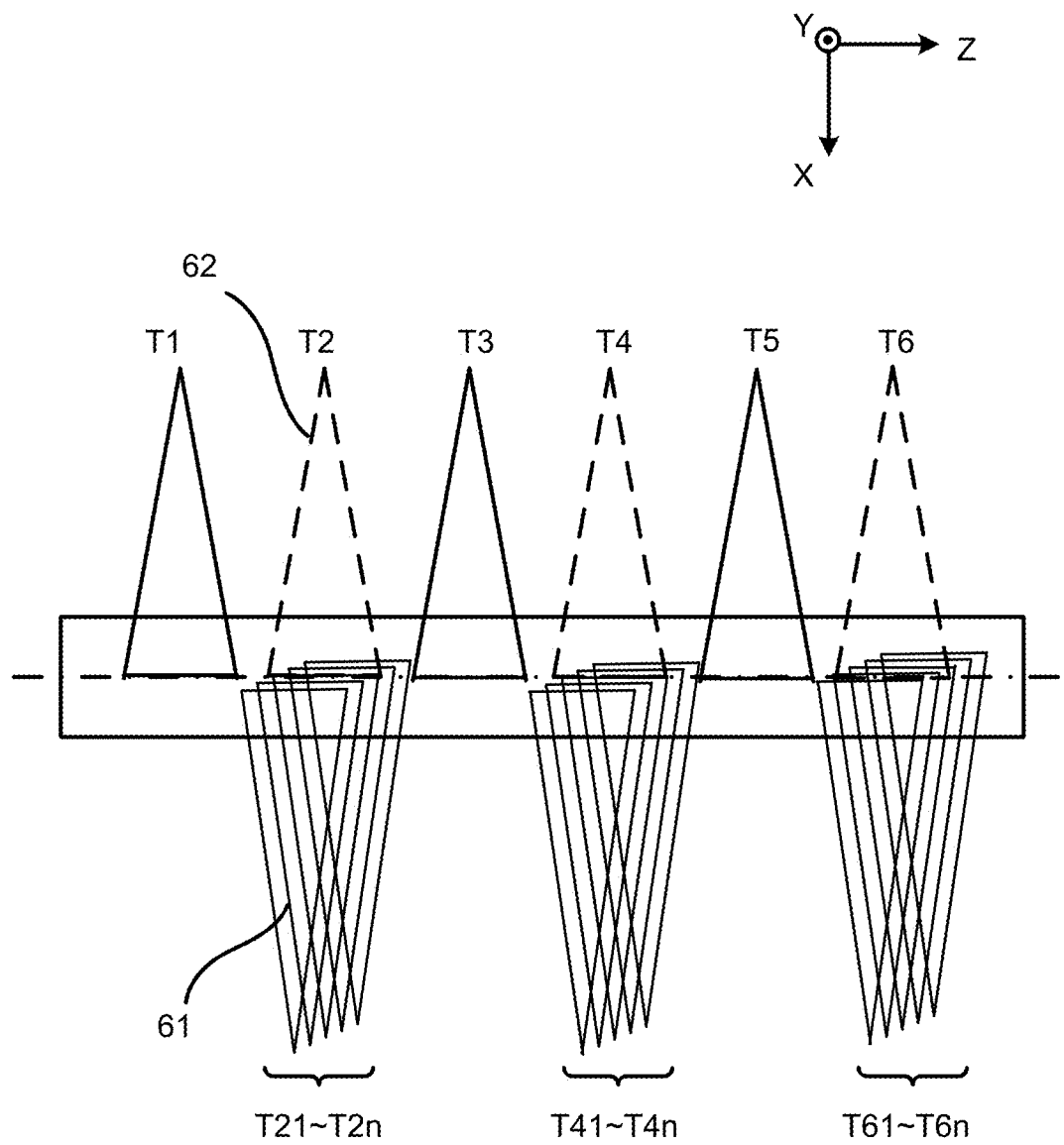
FIG. 6 is a schematic diagram of the insertion of equivalent projection data extracted from back projection data into forward projection data according to an exemplary embodiment.

After being extracted, equivalent projection data can be inserted into corresponding projection data in the forward target scanning direction. FIG. 6 is a schematic diagram of the insertion of equivalent projection data extracted from back projection data into forward projection data in the embodiments of the present application. As shown in FIG. 6, the radiographic source 20 rotates to the target scanning direction at the time points T1, T3, and T5 and rotates to the opposite direction range of the target scanning direction at the time points T21 to T2n, T41 to T4n, and T61 to T6n. Projection data used to simulate the ray beam 62 emitted from the radiographic source 20 in the target scanning direction at the time point T2 can be extracted from corresponding projection data of a plurality of ray beams 62 at the time points T21 to T2n. It should be noted that the ray beam 62 is actually not emitted from the radiographic source 20 in the target scanning direction at the time point T2. The ray beam 62 is obtained by simulating the ray beams in the opposite direction, and therefore is denoted by dashed lines. Alike, projection data used to simulate the ray beam emitted from the radiographic source 20 in the target scanning direction at the time points T4 and T6 can be extracted respectively from corresponding projection data of a plurality of ray beams at the time points T41 to T4n and T61 to T6n. The time points T2, T4, and T6 are time points of T21 to T2n, T41 to T4n and T61 to T6n, respectively. In this way, in the solution where the use of projection data in two opposite directions can be equivalent to the use of projection data only in one direction, if other parameters are the same, projection data in the target scanning direction can be obtained when the moving speed of the scanning table 40 is only half the moving speed of the scanning table 40 in the embodiments of the present application. Therefore, it takes a shorter time to complete a scout scan in the embodiments of the present application.

In this way, after the paths of rays in the opposite direction are considered, an extraction of projection data used to simulate a forward scan from back projection data can improve the image quality of a scout image.

When equivalent projection data is extracted, different extraction methods can be used to extract a collection of different projection data, as required. In some embodiments, for a plurality of scanning directions in a preset direction range, corresponding line projection data of one ray sub-beam can be extracted from corresponding projection data in each scanning direction of the plurality of scanning directions and the extracted line projection data is re-sorted to obtain equivalent projection data. The ray sub-beam may be a collection of rays of the ray beam emitted from the radiographic source 20 in the scanning direction, with the included angle between the projection of the rays on the plane of the gantry 10 and the plane where the scanning table 40 is located within a preset angle range. The angle range of each ray sub-beam depends on the accuracy required for a scout image. The scanning angle (namely, the angle of the projection of a ray beam on the plane of the gantry 10) of the radiographic source 20 can be divided in advance to obtain a plurality of preset angle ranges. In some embodiments, a preset angle range can be small, and in this case, the projection of a ray sub-beam on the plane of the gantry 10 may be approximate to a line. That is to say, viewed from the direction of the Z-axis, each ray sub-beam is approximate to a line, and therefore, the projection data here is called line projection data for short. A plurality of scanning directions in a preset direction range may be a plurality of scanning directions selected at intervals of a preset angle from the preset direction range. The interval may be determined according to the requirements, for example, according to the amount of calculations, the accuracy of a scout image and other factors. In this way, in the direction range of the direction opposite to a target direction, a ray sub-beams within a specific angle range are selected respectively from a plurality of ray beams emitted from the radiographic source, and the projection data of these ray sub-beams are re-sorted to obtain equivalent projection data in the target direction. The extraction and re-sorting of fine-grain data in units of ray sub-beams can improve the image quality of a scout image.

In the embodiments, according to the shape of the ray beams to be reconstructed, the preset angle range adopted for the extraction of line projection data may be a different angle range set for each scanning direction respectively, or the same angle range set uniformly.

For example, line projection data of a corresponding ray sub-beam in one angle sub-range of the angle range covered a ray beam emitted from the radiographic source in the second scanning direction may be extracted from corresponding projection data in the scanning direction, wherein the plurality of scanning directions correspond to different angle sub-ranges, respectively. In this way, the extracted ray sub-beams have different directions and the projection data of divergent ray beams simulated and emitted from the radiographic source in the target scanning direction can be constructed by re-sorting the projection data thereof. Thus, the image quality of the obtained scout image is equivalent to the quality of the scout image generated by use of a traditional method.

Figure 7:
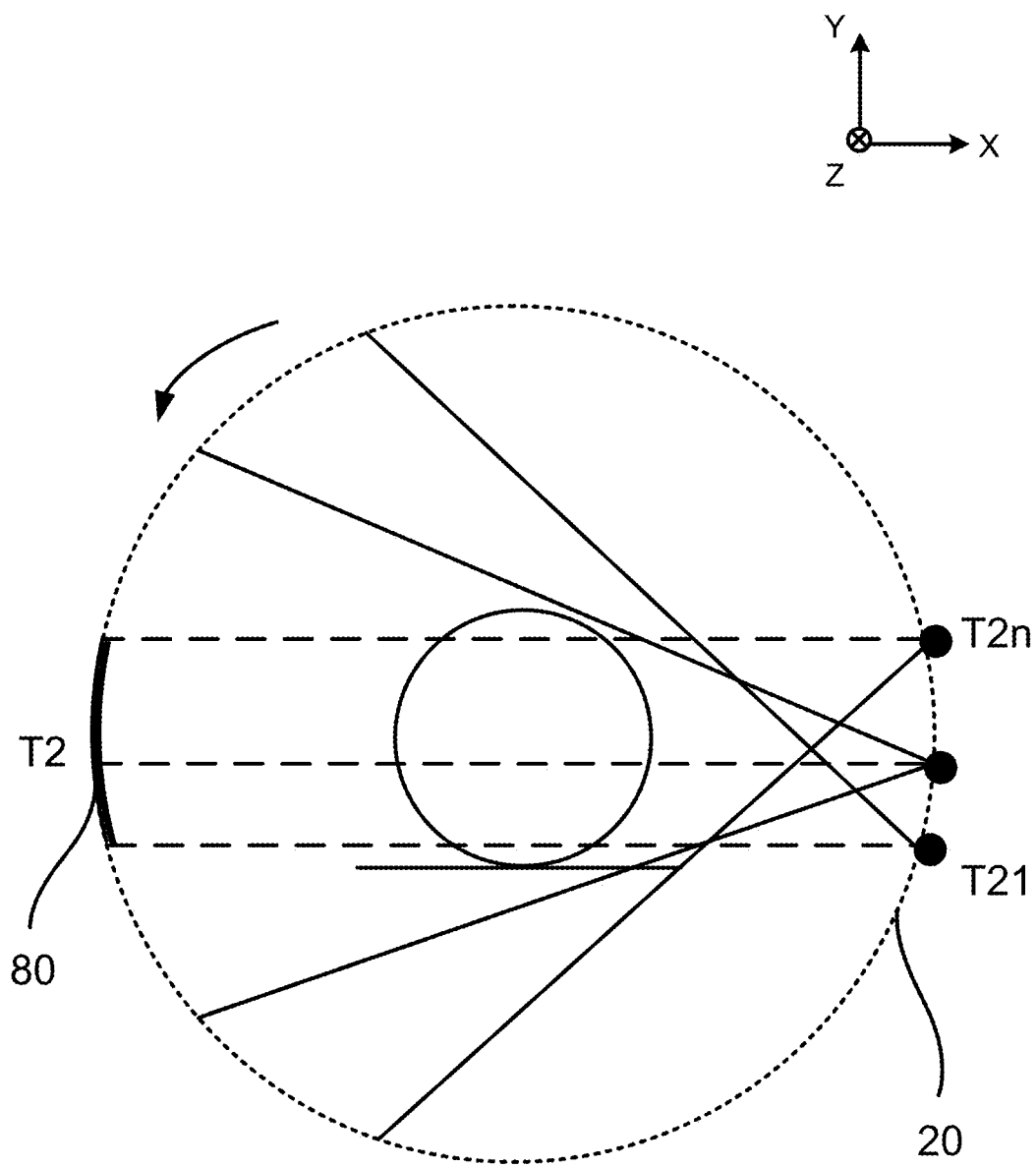
FIG. 7 is a schematic diagram of the extraction of equivalent projection data according to an exemplary embodiment.

Again for example, corresponding line projection data of ray sub-beams having the same preset angle range may be extracted respectively from corresponding projection data in a plurality of scanning directions. FIG. 7 is a schematic diagram of the extraction of equivalent projection data in the embodiments of the present application. As shown in FIG. 7, projection data of ray sub-beams having the same preset angle range may be extracted from ray beams emitted from the radiographic source 20 at the time points T21 to T2n. For the sake of simplicity, ray sub-beams are approximate to a line and are denoted by dashed lines in FIG. 7. In this way, the projection data of extracted ray sub-beams may be equivalent to corresponding projection data of parallel ray beams emitted from a virtual parallel radiographic source 80 at the time point T2. The same angle range may be centered at the second scanning direction. That is to say, the approximate direction of the extracted ray sub-beams is the direction of a vertical line from the center of the radiographic source 20 to the axis of rotation of the radiographic source 20 when a scan starts from the target scanning direction, or the expected scanning angle of a scout image. In this way, by extracting corresponding projection data of near-parallel ray sub-beams, a size deviation brought about by divergent ray beams to a scanned object in the scout image when the position of the scanned object deviates from the rotating center of the radiographic source may be avoided, and thus the result of the estimated dose is more accurate.

An example is given below to illustrate the generation process of a scout image.

For example, the medical imaging device is a computed tomography (CT) device and it is assumed that the original projection data the detector 30 obtains for a ray beam is $S(\beta_{CH}, \beta_{Row}, \alpha)$, wherein $\beta_{CH}$ represents the angle of a CT ray beam in the channel direction (namely, the direction perpendicular to the Z-axis) of the detector 30 and $\beta_{Row}$ represents the angle of a CT ray beam in the row direction (namely, the direction of the Z-axis) of the detector 30. The accumulated angle of rotation of the tube (namely, the radiographic source 20 of the CT device) is $$\alpha = \alpha_0 + n \cdot \Delta\alpha \quad (1)$$

wherein, $\Delta\alpha$ is the exposure angle of each reading at the time of scanning, or the corresponding scanning angle of each original projection datum.

The acquired original data and the data obtained after further processing of the original distribution of the detector channels and sector beam geometries are re-sorted and values are interpolated according to the rotation speed of the gantry 10 and the moving speed of the scanning table 40 to calculate a scout image.

For each projection datum, a correlation exists between the Z-axis position of a projection with an angle of $\alpha$ and scanning parameters (for example, collimated width $W_{coll}$ in the Z-axis direction, corresponding feed (also known as pitch Pf of the scanning table 40 for each revolution of the gantry 10, and total number of revolutions $N_{rd}$ by the end of the current scan).

Then the axial position of projection data can be calculated as:

$$Z(\alpha) = Z_0 + \frac{(\alpha - \alpha_0) \cdot W_{coll} \cdot Pf}{\Delta\alpha \cdot N_{rd}} \quad (2)$$

The Z-axis position of data in each row in the same projection data is:

$$Z(\beta_{ROW}, \alpha) = Z_0 + \frac{(\alpha - \alpha_0) \cdot W_{coll} \cdot Pf}{\Delta\alpha \cdot N_{rd}} + R_f \cdot \tan(\beta_{ROW}) \quad (3)$$

wherein, $W_{coll}$ represents the width of a collimated X-ray beam, Pf is the pitch, and $W_{coll} \cdot Pf$ is the distance the scanning table moves for each revolution.

Through the above-mentioned calculation, for projection data of each sector X-ray beam with an angle of $\alpha$, each original data element can be located on the Z-axis according to formula (3). Then, preset Z-axis grids can be used to convert projection data into $D(\theta_{CH}, Z, \alpha)$ to generate a scout image.

In some examples, when ray beams emitted from the radiographic source 20 in the forward direction are simulated, elements of a scout image can directly be obtained from projection data by interpolating values between adjacent angles and adjacent Z-axis positions according to the geometries of ray beams.

$$LR(x, Z, \alpha) = D(\theta_{CH}, Z, \alpha) \quad (4)$$

For a scan with the pitch factor greater than 1.0, $LR(x, Z, \alpha)$ has data slits on the Z-axis. Equivalent projection data extracted from the opposite direction range (namely, the first direction range) can be used to fill up the data slits.

$$LR_{RR}(x, Z, \alpha) = f(\beta_{CH}, \beta_{ROW}, \alpha), Z(\beta_{ROW}, \alpha), RB(\alpha, \theta_{CH})) \quad (5)$$

That is to say, when the radiographic source 20 is in the opposite direction range, the scout image data comes from a function of back projection data, and the Z-axis positions of the projection data are calculated according to the function of the angle of the tube and the row of the detector and the function of the angle of the tube and the number of channels.

Therefore, the output scout image may be a merged image obtained from the direct reading $LR_{DR}(x, Z)$ and the reverse reading $LR_{RR}(x, Z)$.

$$LR_{final}(x, Z, \alpha) = LR_{DR}(x, Z, \alpha) + LR_{RR}(x, Z, \alpha) \quad (6)$$

In addition, when the detector 30 is in two opposite positions on the gantry 10, the direction of the sensor array is opposite. Therefore, when equivalent projection data is obtained, extracted line projection data needs to be re-sorted. For example, extracted corresponding point projection data of points of each ray sub-beam may be re-sorted in a reverse order. Again for example, the projection data of each ray sub-beam may be re-sorted in the corresponding order of the angles of the ray sub-beams in a second scanning direction. It can be seen that since the scanning direction is different, the order of projection data is different and the order of the ray sub-beams extracted from ray beams in different scanning directions is also different from the order of the ray sub-beams of the simulated ray beam in the target direction. Equivalent projection data in the target direction can correctly be reconstructed by re-sorting the projection data.

Figure 8:
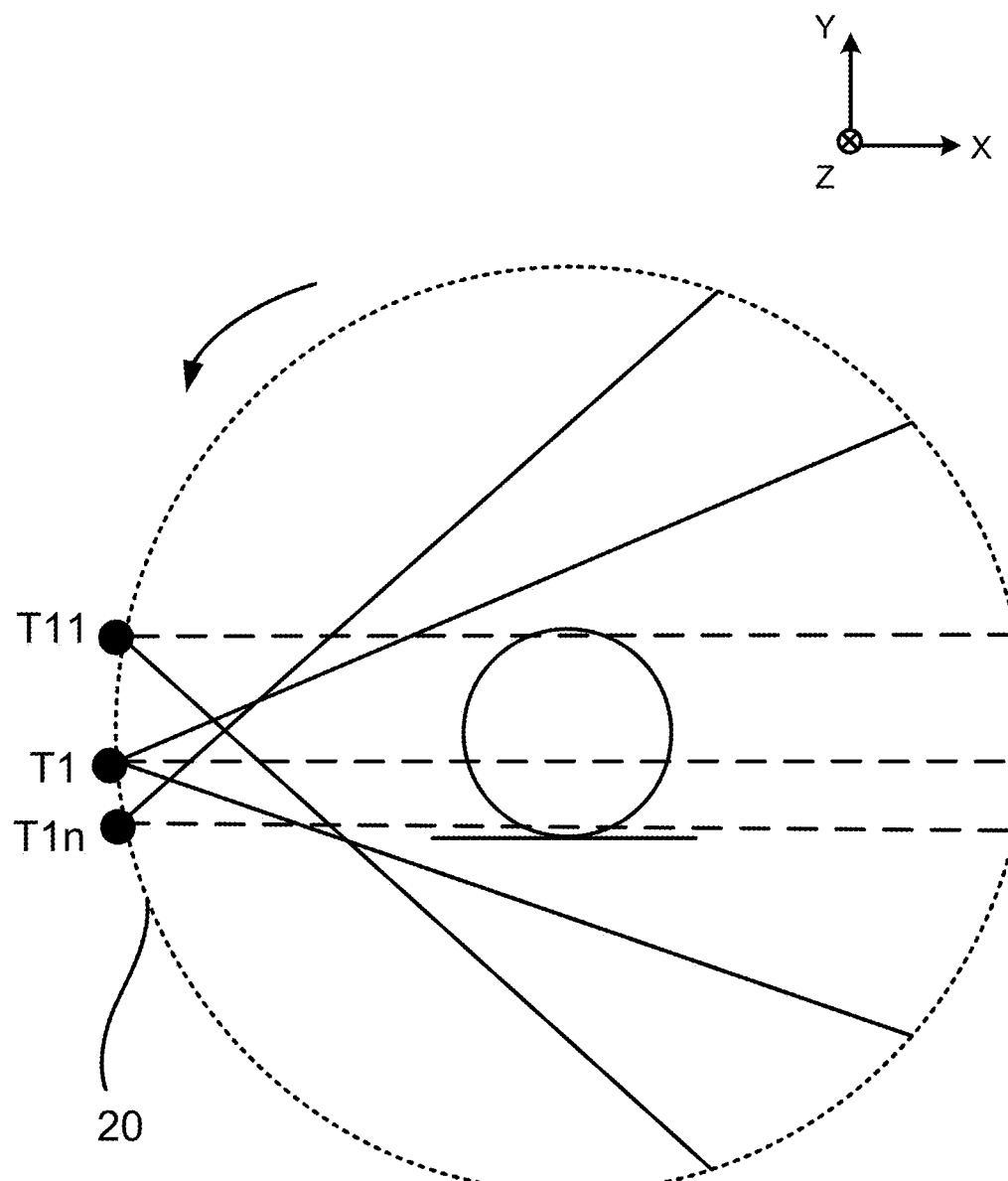
FIG. 8 is a schematic diagram of the extraction of recombined projection data in the embodiments of the present application.

In some embodiments, forward projection data may also be extracted from corresponding projection data in each scanning direction in a direction range of the target scanning direction. That is to say, corresponding recombined projection data in a second scanning direction is extracted as corresponding projection data in the second scanning direction from corresponding projection data in a second preset direction range of the second scanning direction. FIG. 8 is a schematic diagram of the extraction of recombined projection data in the embodiments of the present application. As shown in FIG. 8, projection data of a ray sub-beam (denoted by dashed lines in the figure) may be extracted respectively from projection data of a plurality of ray beams emitted from the radiographic source 20 at the time points t11 to T1$n$. The ray sub-beam may be a collection of rays of the ray beam in one scanning direction, with the included angle between the projection of the rays on the plane of the gantry and the plane where the scanning table is located within a preset angle range. The angle range of a ray sub-beam extracted in each scanning direction of a plurality of scanning directions may be an angle range preset for each scanning direction respectively, or the same angle range set uniformly. By recombining the extracted projection data of ray sub-beams, ray beams which actually do not exist and are emitted from the radiographic source 20 at the time point T1 in the required shape can be simulated. T1 is a time point between T11 and T1$n$. Similar "equivalent projection data" and "recombined projection data" is actually not completely consistent with the projection data produced by the ray beam in the target scanning direction because the corresponding Z-axis position of each ray beam emitted between the time point T11 and the time point T1$n$ is different. "Recombined projection data" obtained by combining projection data in which Z-axis positions are slightly different is a simulation of projection data produced by a distorted ray beam in the target scanning direction. For example, the projection produced by the ray beam emitted from the radiographic source 20 is a rectangle, and the corresponding projection of recombined projection data extracted from a plurality of ray beams in the forward direction may be a parallelogram. For recombined projection data whose projection is a parallelogram, data can be extracted from other data to patch the parallelogram into a rectangle, or some of recombined projection data may be discarded to cut the parallelogram into a rectangle to obtain the finally used recombined projection data. In this way, by extracting projection data from projection data of a plurality of ray beams in one direction range and recombining the data into simulated projection data of the ray beam emitted from the radiographic source in the target direction, ray beams emitted from the radiographic source in the target position in any shape can be simulated to meet different requirements.

In some embodiments, considering that a parallel ray beam can avoid a scanned object from being distorted, when recombined data is extracted, corresponding second line projection data of ray sub-beams having the same angle range may be respectively extracted from corresponding projection data in a plurality of scanning directions in a second preset direction range of a second scanning direction, and the second line projection data is combined to obtain recombined projection data. For example, the same angle range may be centered at the second scanning direction. In this way, by extracting corresponding projection data of parallel ray sub-beams, a size deviation brought about by divergent ray beams to the scanned object in the scout image when the position of the scanned object deviates from the rotating center of the radiographic source may be avoided.

Figure 9:
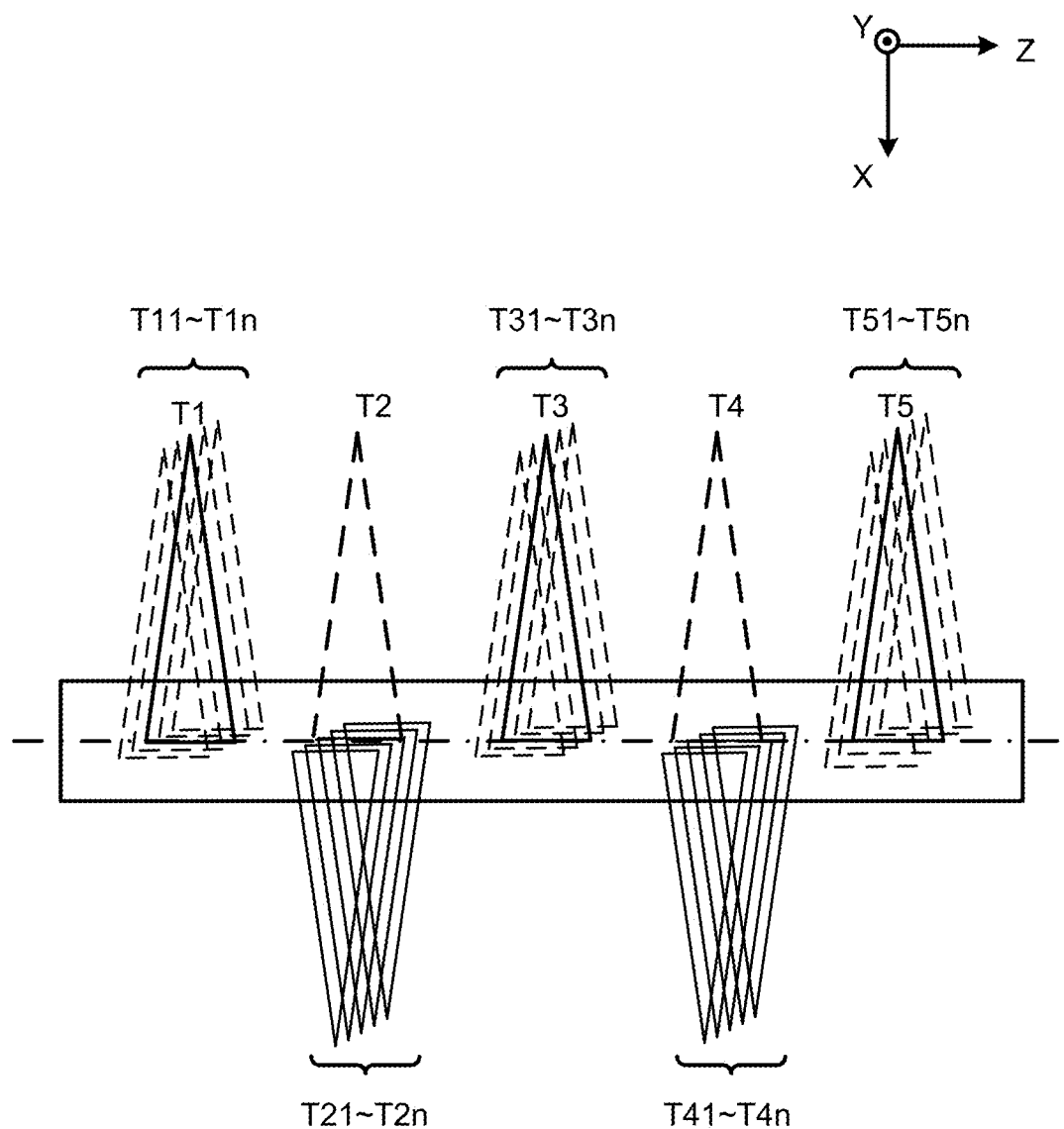
FIG. 9 is a schematic diagram of the re-sorting of projection data according to an exemplary embodiment.

In the embodiments, when simulated projection data are inserted into corresponding projection data in the second scanning direction, equivalent projection data and the corresponding projection data in the second scanning direction can be arranged in the order of the scan time of the data. The scan time of equivalent projection data extracted from the back projection data (namely, projection data in the first preset direction range of the first scanning direction) is the scan time of the back projection data. When forward projection data is recombined projection data, the scan time of recombined projection data is the corresponding scan time of the forward projection data (namely, projection data in the second preset direction range of the second scanning direction). FIG. 9 is a schematic diagram of the re-sorting of projection data in the embodiments of the present application. As shown in FIG. 9, recombined projection data is extracted from projection data of a plurality of ray beams (denoted by dashed lines) emitted at the time points T11 to T1$n$, T31 to T3$n$ and T51 to T5$n$ and is used to simulate projection data of ray beams (denoted by solid lines) which actually do not exit and are emitted from the radiographic source 20 at the time points T1, T3 and T5. Equivalent projection data is extracted from projection data of a plurality of ray beams (denoted by solid lines) emitted at the time points T21 to T2$n$ and T41 to T4$n$ and is used to simulate projection data of ray beams (denoted by dashed lines) which actually do not exit and are emitted from the radiographic source 20 at the time points T2 and T4. The projection data is re-sorted according to the scan time and is used as spiral scanning data of the scanned object to generate a scout image of the scanned object.

An example is given below to illustrate the generation process of a scout image by using parallel ray beams.

For example, as far as the above-mentioned CT device is concerned, through calculations according to formulas (1), (2) and (3), for projection datum of each sector X-ray beam with an angle of $\alpha$, each original data element can be located on the Z-axis according to formula (3).

Then, preset Z-axis grids can be used to convert projection data into $D(\theta_{CH}, Z, \alpha)$ to generate a scout image.

In some examples, when parallel ray beams emitted from the radiographic source 20 in the forward direction are simulated, projection data can be converted, for example, from a sector geometry into a parallel geometry, and is then re-sorted, and the corresponding scout image at the target scanning angle is derived:

$$LR(x,Z,\theta)=D(\beta_{CH},Z,\alpha) \quad (4)$$

wherein, $(x, Z, \theta)$ is a function of $(\beta_{CH}, Z, \alpha)$, namely, a process of recombination of a parallel beam.

For a scan with the pitch factor greater than 1.0, $LR(x, Z, \theta)$ has data slits on the Z-axis. Equivalent projection data extracted from the opposite direction range (namely, the first direction range) is used to fill up the data slits.

$$LR_{RR}(x,Z,\theta)=LR(x,Z,\theta+180°) \quad (5)$$

Therefore, the output scout image may be a merged image collection obtained from the direct projection data $LR_{DR}$ (x, Z) and the equivalent projection data $LR_{RR}$ (x, Z).

$$LR_{final}(x,Z,\theta)=LR_{DR}(x,Z,\theta)+LR_{RR}(x,Z,\theta) \qquad (6)$$

To further shorten the generation time of a scout image, the interpolation method can be used to obtain an area which scanning data does not cover. That is to say, interpolation data calculated according to the equivalent projection data and corresponding projection data in the second scanning direction is inserted in a position where the equivalent projection data and the projection data in the second scanning direction are spliced. In this way, by interpolating values in the areas not covered by projection data in two opposite directions, the generation time of the scout image may be further shortened.

Figure 10:
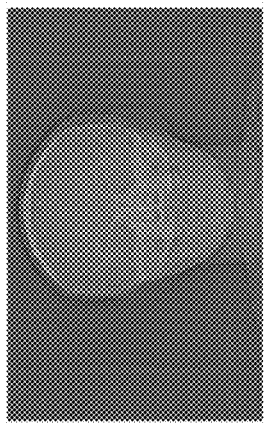
FIG. 10 shows comparisons between scout images generated by use of the medical image generation method according to exemplary embodiments and traditional scout images.
Figure 10:
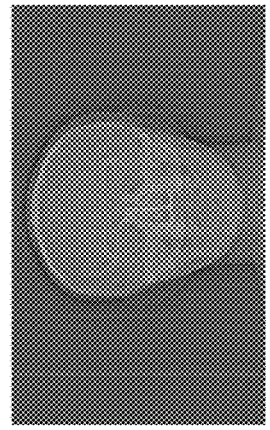
Figure 10:
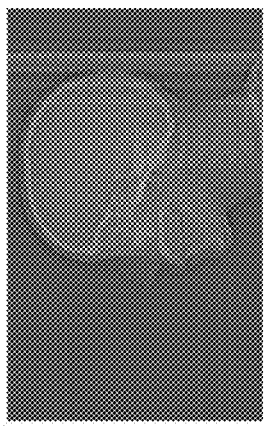
Figure 10:
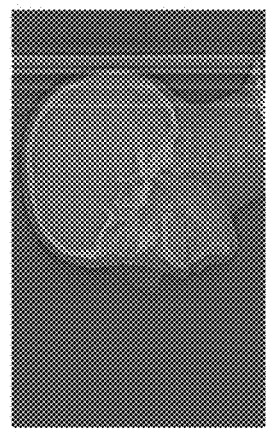
Figure 10:
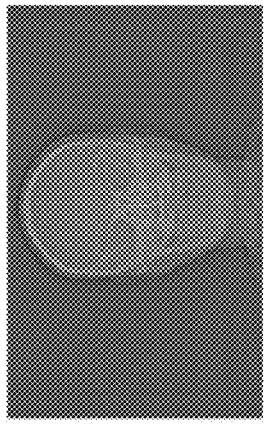
Figure 10:
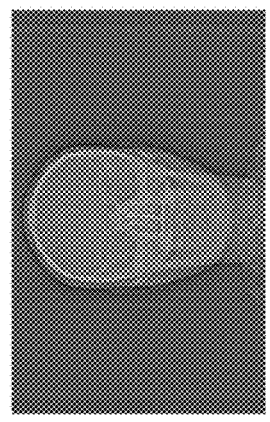

FIG. 10 shows comparisons between scout images generated by use of the medical image generation method in the embodiments of the present application and traditional scout images. As shown in FIG. 10, for scout scans of a head model at three angles, compared with traditional scout images (in the upper row), the scout images (in the lower row) generated by using the methods in the embodiments of the present application, setting the parameters properly (for example, the pitch factor is 2.0) and utilizing rotating projections have an equivalent image quality.

The above-mentioned description is based on the generation of a scout image in a target scanning direction. When scout images at a plurality of angles need to be generated, a plurality of scout scans are not required, projection data in each target scanning direction and the opposite direction is extracted from projection data obtained from one spiral scan, and the scout image in each target scanning direction is obtained according to the methods in the embodiments. The generation of scout images is not described here again.

It can be seen that only projection data in two direction ranges needs to be used in the methods provided by the present application. Therefore, selective exposures are allowed so that the scanning dose can be reduced. For example, by modulating the current supplied to the radiographic source, the radiographic source can emit rays in a first preset direction range of the first scanning direction and a second preset direction range of the second scanning direction, but will not emit rays beyond the first preset direction range and the second preset direction range. In this way, the radiographic source is enabled to emit rays only in the direction range where projection data needs to be acquired. Thus, the radiation dose a scanned object receives during a scout scan is reduced and the influence of radiation on the health of the scanned object is alleviated.

Figure 11:
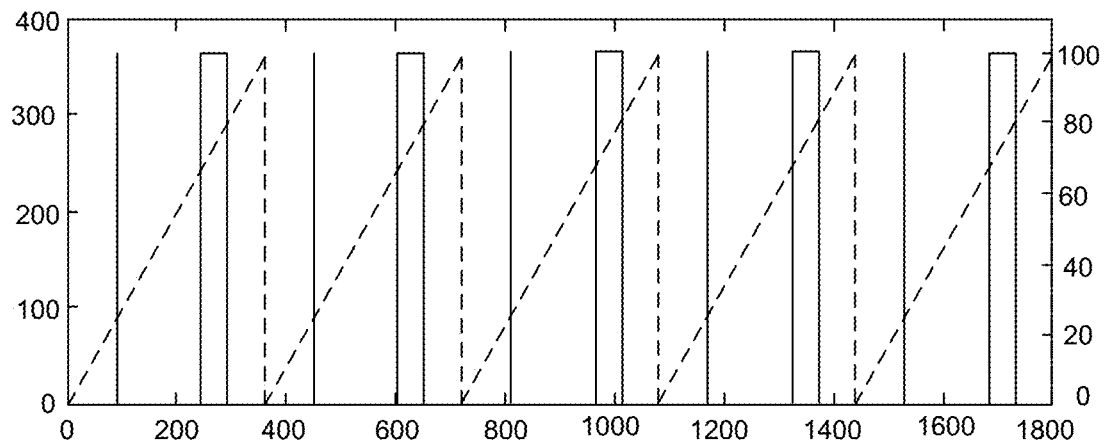
FIG. 11 is a schematic diagram of the modulation of the current supplied to the radiographic source according to exemplary embodiments.

For example, the exposure control triggered by the angle of rotation of the gantry for the radiographic source, or the radiographic source output calculated by the system time sequence and the corresponding ray output function of the system time may be based on the tube current modulation oriented to the angle of rotation of the gantry. The dose based on a rotary scout scan may be up to the level of a conventional procedure, and in addition, the advantages of the rotary scout scan are still kept. FIG. 11 is a schematic diagram of the modulation of the current supplied to the radiographic source in the embodiments of the present application. As shown in FIG. 11, the angle range to be scanned is an angle of sector of an image range consisting of an angle and ±½ of the angle requiring scout images. The angle of sector is determined by the required ray beam shape. For example, the angle of sector may be an opening angle of the required ray beam shape in the channel direction (namely, the direction perpendicular to the Z-axis) of the detector 30. Therefore, current modulation may be a way of controlling the exposure switch or changing the current during the rotation of the gantry. The waveform produced from current modulation may be a pulse wave, square wave, sine wave or a combination thereof. For example, a pulse wave is used in a target scanning and a square wave is used in the opposite direction range. As shown in FIG. 11, the horizontal axis represents the accumulated angle of rotation of the radiographic source 20, the vertical axis on the left represents the angle of the radiographic source 20 in the gantry 10, and the vertical axis on the right represents the intensity of the output current.

In one example, the above-mentioned current modulation solution is adopted. When the pitch factor (namely, the corresponding feed of the scanning table 40 for each revolution of the gantry 10) is set to 3.0, even if the preset ray exposure current is low, the dose will still be higher than in a traditional scout scan mode. Table 1 compares the parameters of a traditional A.P./P.A scout scan and Lat. scout scan with the parameters of the rotary scout scan with different pitch factors Pf in the present application.

TABLE 1

| Report on scan time and dose of scans by SOMATOM Go. Now | | | | | |
|---|---|---|---|---|---|
| | Scan Time | Voltage | Current | CTDI vol. (16 cm) | DLP |
| A.P./P.A scout scan | 2.04 s | 130 kV | 30 mA | 0.25 mGy | 6 mGyem |
| Lat. scout scan | 2.04 s | 130 kV | 30 mA | 0.25 mGy | 6 mGyem |
| Rotary scout scan (Pf 4.0) | 4.72 s | 130 kV | 15 mA | 0.72 mGy | 19 mGyem |
| Rotary scout scan (Pf 3.0) | 6.02 s | 130 kV | 15 mA | 0.96 mGy | 24 mGyem |
| Rotary scout scan (Pf 2.0) | 8.99 s | 130 kV | 15 mA | 1.44 mGy | 36 mGyem |
| Rotary scout scan with current modulation (Pf 3.0) | 6.02(3.34) s | 130 kV | 15 mA | 0.53 mGy | 13.3 mGyem |

However, a rotary scout scan with current modulation can be used to reduce the dose (see the parameters in the last column in Table 1). For example, when scout images at angles of 0°, 90°, 180° and 270° are provided, projection data can be acquired from a limited scout scan range to generate a plurality of scout images during a scan. For each scout image, the dose may be $$CTDL_{TCM} = 2 \cdot \frac{\text{Range}_{tube}}{180} \cdot CTDL_{Full} \quad (7)$$

$\text{Range}_{tube}$ represents each direction range to be scanned. Here, a scout image in a single direction can be obtained from projection data in two opposite directions, and therefore each scout image requires projection data in two directions. In this case, $\text{Range}_{tube}$ is about 50°, and therefore when scout images at two angles are simultaneously generated, $DLP_{TCM}$ is estimated to be 13.33 mGycm. This is equivalent to 12 mGycm in an A.P. scout scan or a Lat. scout scan.

Figure 12:
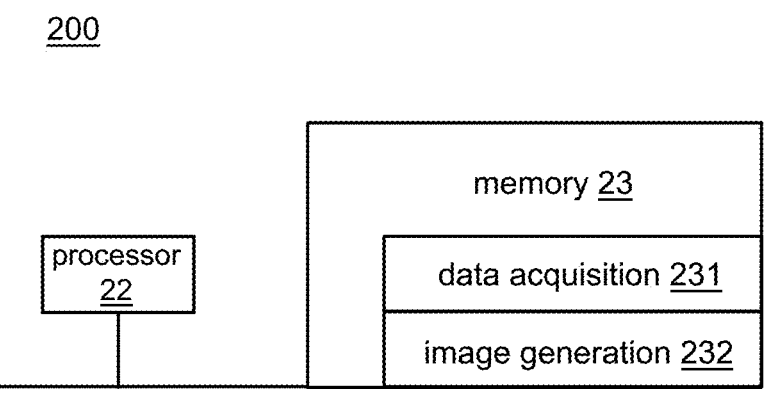
FIG. 12 is a schematic diagram of the image generation apparatus according to an exemplary embodiment.

The embodiments further provide a medical image generation apparatus. FIG. 12 is a schematic diagram of the image generation apparatus 200 in the embodiments of the present application. As shown in FIG. 12, the image generation apparatus 200 may comprise a data acquisition module 231 and an image generation module 232, wherein, the data acquisition module 231 can acquire projection data of a scanned object during the rotation of a radiographic source, and the image generation module can perform data splicing in the moving direction of the scanning table for corresponding projection data in two opposite scanning directions to obtain a scout image of the scanned object.

In some embodiments, the medical image generation apparatus 200 may further comprise a processor 22 and a memory 23. The data acquisition module 231 and the image generation module 232 are stored in the memory 23 in the form of computer-readable instructions, and the instructions enable the processor 22 to execute the functions of the data acquisition module 231 and the image generation module 232 to implement the methods in the embodiments.

It should be noted that not all the steps or modules in the above-mentioned processes and structural diagrams are required, and some steps or modules can be ignored, depending on the actual requirements. The execution sequence of the steps is not fixed and may be adjusted as required. The partition of the modules is a functional partition for the convenience of description. In the practical implementation, the function of a module may be realized by a plurality of modules, and the functions of a plurality of modules may be realized by one module and these modules may be located in the same equipment or may be located in different equipment. In addition, "first" and "second" used in the previous description only conveniently distinguish between two objects having the same meaning, but do not represent any substantive difference.

The modules in the embodiments may be implemented in the form of hardware or in the form of a hardware platform and software. The above-mentioned software comprises machine-readable instructions and is stored in a non-volatile storage medium. Therefore, the embodiments may also be software products.

In the embodiments, hardware may be special hardware or hardware executing machine-readable instructions. For example, hardware may be a specially designed permanent circuit or logic device (for example, application-specific processor such as field programmable gate array (FPGA) or application specific integrated circuit (ASIC)) to complete specific operations. Hardware may also comprise a programmable logic device or circuit (for example, general processor or other programmable processor) temporarily configured by software to perform specific operations.

The corresponding machine-readable instructions of the modules in the drawings can enable the operating system on a computer to complete a part or all of the operations described here. The non-volatile computer-readable storage medium may be a memory set in an extension board inserted into a computer or a memory set in an extension unit connected with a computer. A CPU installed on the extension board or extension unit can perform a part or all of the actual operations according to instructions.

The non-volatile computer-readable storage medium includes a floppy disk, hard disk, magneto-optical disk, compact disk (for example, compact disk read-only memory (CD-ROM)), compact disk-recordable (CD-R), compact disk-rewritable (CD-RW), digital video disk-read only memory (DVD-ROM), digital versatile disk-random access memory (DVD-RAM), digital versatile disk+recordable and rewritable (DVD+RW), magnetic tape, non-volatile memory card, and read-only memory (ROM). Alternatively, the program codes may be downloaded from the server computer over a communication network.

In a word, the scope of the claims should not be limited to the implementation modes in the above-mentioned examples and a broadest interpretation should be given to the description as a whole.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

Hardware may include circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

REFERENCE LIST

100 Scanning apparatus
10 Gantry
20 Radiographic source
30 Detector
40 Scanning table
200 Medical image generation apparatus
50 Scout image generator
60 Tomographic image generator
S31, S32, S41, S42 Steps
51, 53 Ray beams
52 Ray
T1, T2, T3, T4, T5, T6, T21, Tm, T11, T1$n$, T2$n$, T31, T3$n$, T41, T4$n$, T51, T5$n$, T61, T6$n$ Time points
80 Virtual parallel radiographic source
231 Data acquisition module
232 Image generation module
22 Processor
23 Memory

The invention claimed is:

1. A medical image generation method, comprising:
acquiring projection data of a scanned object during rotation of a radiographic source; and
generating a scout image of the scanned object in one scanning direction using corresponding projection data in two opposite scanning directions in the projection data, generating the scout image including extracting corresponding equivalent projection data in a second scanning direction from the corresponding projection data in a first direction range of a first scanning direction and inserting equivalent projection data into the corresponding projection data in the second scanning direction, wherein the second scanning direction is opposite to the first scanning direction, the one scanning direction being used to represent a relative position relationship between the radiographic source and the scanned object, wherein extracting the corresponding equivalent projection data includes:
for each scanning direction of a plurality of scanning directions in the first direction range, extracting corresponding line projection data of one ray sub-beam from the corresponding projection data in the scanning direction, the ray sub-beam being a collection of rays of ray beam emitted from the radiographic source in the scanning direction, with an included angle between the projection of the rays on a plane of a gantry and a plane where a scanning table is located within a preset angle range, and
re-sorting the extracted line projection data to obtain the equivalent projection data.

2. The method as claimed in claim 1, wherein extracting the corresponding line projection data of the one ray sub-beam comprises:
extracting line projection data of a corresponding ray sub-beam in one angle sub-range of the angle range covered a ray beam emitted from the radiographic source in the second scanning direction from the corresponding projection data in the scanning direction, wherein the plurality of scanning directions correspond to different angle sub-ranges, respectively.

3. The method as claimed in claim 1, wherein extracting the corresponding line projection data of one ray sub-beam comprises:
extracting the corresponding line projection data of ray sub-beams having a same preset angle range respectively from the corresponding projection data in the plurality of scanning directions.

4. The method as claimed in claim 3, wherein the same angle range is centered at the second scanning direction.

5. The method as claimed in claim 1, wherein re-sorting the extracted line projection data comprises:
re-sorting the extracted corresponding point projection data of points of each ray sub-beam in a reverse order, and
re-sorting the projection data of each ray sub-beam in the corresponding order of the ray sub-beams in a second scanning direction.

6. The method as claimed in claim 1, further comprising:
extracting corresponding recombined projection data in a second scanning direction as corresponding projection data in the second scanning direction from corresponding projection data in a second direction range of the second scanning direction.

7. The method as claimed in claim 6, wherein extracting the corresponding recombined projection data in a second scanning direction comprises:
for a plurality of scanning directions in the second direction range, extracting corresponding second line projection data of one ray sub-beam respectively from corresponding projection data in each scanning direction of the plurality of scanning directions, wherein the ray sub-beam is a collection of rays of the ray beam emitted from the radiographic source in the scanning direction, with the included angle between the projection of the rays on the plane of the gantry and the plane where the scanning table is located within a preset angle range, and
combining second line projection data to obtain the recombined projection data.

8. The method as claimed in claim 7, wherein the same angle range is centered at the second scanning direction.

9. The method as claimed in claim 1, further comprising:
inserting interpolation data calculated in the equivalent projection data and corresponding projection data in the second scanning direction in a position where the equivalent projection data and the projection data in the second scanning direction are spliced.

10. The method as claimed in claim 1, further comprising:
modulating current supplied to the radiographic source to control an intensity of rays emitted from the radiographic source in a first direction range of the first scanning direction and a second direction range of the second scanning direction greater than an intensity of rays emitted in directions beyond the first direction range and the second direction range.

11. A non-transitory computer-readable storage medium with an executable program stored thereon, that when executed, instructs a processor to perform the method of claim 1.

12. A medical image generation apparatus, comprising:
a memory storing computer-readable instructions; and
a processor that is configured to execute the instructions to perform the method of claim 1.

13. A medical image generation system, comprising:
a scanner configured to acquire projection data of a scanned object during rotation of a radiographic source; and
an image generator configured to generate a scout image of the scanned object in one scanning direction based on corresponding projection data in two opposite scanning directions in the projection data, the generating the scout image including extracting corresponding equivalent projection data in a second scanning direction from the corresponding projection data in a first direction range of a first scanning direction and inserting equivalent projection data into the corresponding projection data in the second scanning direction, wherein the second scanning direction is opposite to the first scanning direction, wherein extracting the corresponding equivalent projection data includes:
for each scanning direction of a plurality of scanning directions in the first direction range, extracting corresponding line projection data of one ray sub-beam from the corresponding projection data in the scanning direction, the ray sub-beam being a collection of rays of ray beam emitted from the radiographic source in the scanning direction, with an included angle between the projection of the rays on a plane of a gantry and a plane where a scanning table is located within a preset angle range, and
re-sorting the extracted line projection data to obtain the equivalent projection data.

14. A medical image generation method, comprising:
acquiring projection data of a scanned object during rotation of a radiographic source;
generating a scout image of the scanned object in one scanning direction using corresponding projection data in two opposite scanning directions in the projection data, the generating the scout image including extracting corresponding equivalent projection data in a second scanning direction from the corresponding projection data in a first direction range of a first scanning direction and inserting equivalent projection data into the corresponding projection data in the second scanning direction, wherein the second scanning direction is opposite to the first scanning direction, the one scanning direction being used to represent a relative position relationship between the radiographic source and the scanned object; and
extracting corresponding recombined projection data in the second scanning direction as the corresponding projection data in the second scanning direction from corresponding projection data in a second direction range of the second scanning direction.

15. A medical image generation apparatus, comprising:
a memory storing computer-readable instructions; and
a processor that is configured to execute the instructions to perform the method of claim 14.

* * * * *